United States Patent
Xue et al.

(10) Patent No.: US 9,814,482 B2
(45) Date of Patent: Nov. 14, 2017

(54) ULTRASONIC SURGICAL INSTRUMENT AND ULTRASONIC SURGICAL SYSTEM

(71) Applicants: REACH SURGICAL INC., Tianjin (CN); China Surgical (Shanghai) Corporation, Shanghai (CN)

(72) Inventors: Qingchao Xue, Shanghai (CN); Wugan Hao, Shanghai (CN); Xiaofeng Yang, Shanghai (CN); Meijun Shen, Shanghai (CN); Qizhang Chen, Shanghai (CN)

(73) Assignees: China Surgical (Shanghai) Corporation, Shanghai (CN); REACH SURGICAL, INC., Tianjin (CN)

( * ) Notice: Subject to any disclaimer, the term of this patent is extended or adjusted under 35 U.S.C. 154(b) by 227 days.

(21) Appl. No.: 14/891,995

(22) PCT Filed: May 21, 2014

(86) PCT No.: PCT/CN2014/078001
§ 371 (c)(1),
(2) Date: Dec. 30, 2015

(87) PCT Pub. No.: WO2014/187318
PCT Pub. Date: Nov. 27, 2014

(65) Prior Publication Data
US 2016/0106456 A1    Apr. 21, 2016

(30) Foreign Application Priority Data

May 22, 2013    (CN) .......................... 2013 1 0191109

(51) Int. Cl.
*A61B 17/32*    (2006.01)
*A61B 17/29*    (2006.01)
(Continued)

(52) U.S. Cl.
CPC ...... *A61B 17/320092* (2013.01); *A61B 19/30* (2013.01); *A61B 2017/2929* (2013.01); *A61B 2019/301* (2013.01); *A61B 2090/031* (2016.02)

(58) Field of Classification Search
CPC ....... A61B 17/22012; A61B 17/320068; A61F 9/00745
(Continued)

(56) References Cited

U.S. PATENT DOCUMENTS

2005/0145402 A1    7/2005    Hehli et al.

FOREIGN PATENT DOCUMENTS

| CN | 1745721 A | 3/2006 |
|---|---|---|
| CN | 101262829 A | 9/2008 |

(Continued)

OTHER PUBLICATIONS

International Search Report dated Aug. 15, 2014.

*Primary Examiner* — Melanie Tyson
(74) *Attorney, Agent, or Firm* — Arent Fox LLP; Michael Fainberg

(57) ABSTRACT

Disclosed are an ultrasonic surgical instrument (100) and ultrasonic surgical system; the ultrasonic surgical instrument (100) includes a waveguide (1) rotatable around an axis and in threaded connection with a transducer (200); a force transmission mechanism is in fixed connection with the waveguide (1), which has at least one stress surface (41); a rotatable mechanism includes a pushing mechanism and a rotatable driving mechanism having at least one force applying surface (51), the applying surface (51) and the stress surface (41) are not perpendicular to the axis, and can be engaged with each other; the pushing mechanism provides a pushing force the rotatable driving mechanism towards the force transmission mechanism, and the rotatable driving mechanism can overcome the pushing force when interac- (Continued)

tion force between the applying surface (51) and the stress surface (41) is in excess of a predetermined value.

20 Claims, 3 Drawing Sheets

(51) Int. Cl.
*A61B 19/00* (2006.01)
*A61B 90/00* (2016.01)

(58) Field of Classification Search
USPC ........................................................ 606/169
See application file for complete search history.

(56) References Cited

FOREIGN PATENT DOCUMENTS

| | | | |
|---|---|---|---|
| CN | 102335038 | A | 2/2012 |
| CN | 102755180 | A | 10/2012 |
| CN | 103025264 | A | 4/2013 |
| CN | 103027719 | A | 4/2013 |
| CN | 203328765 | U | 12/2013 |
| DE | 3709824 | A1 | 10/1988 |

ULTRASONIC SURGICAL INSTRUMENT
AND ULTRASONIC SURGICAL SYSTEM

This application is a US National Stage of International Application No. PCT/CN2014/078001, filed on May 21, 2014, designating the United States, and claiming the benefit of Chinese Patent Application No. 201310191109.3, filed with the State Intellectual Property Office of People's Republic of China on May 22, 2013 and entitled "Ultrasonic surgical instrument and ultrasonic surgical system", which is hereby incorporated by reference in its entirety.

FIELD

The present disclosure relates to an ultrasonic surgical instrument, particularly to an ultrasonic surgical instrument integrated with a torque limiting device.

BACKGROUND

An ultrasonic surgical system typically includes a generator, a transducer, cables, an ultrasonic surgical instrument, a foot switch or a hand switch, etc., here the ultrasonic surgical instrument further comprises a handle, a waveguide, and an end effector. When the ultrasonic surgical instrument is actuated by the foot switch or the hand switch, the generator outputs electrical power at a acoustic resonant frequency to the transducer, and the transducer converts the electrical power into mechanical energy that results in ultrasonic vibrations and transmits to the ultrasonic surgical instrument, which further amplifies the vibrations, so as to vaporize tissues, break down hydrogen bonds of proteins, make cells necrotic, and cut tissues or seal vessels, thereby functions of cutting tissue and hemostasis are achieved.

The ultrasonic surgical instrument is in threaded connection with the transducer. However, a stud of the transducer is so small that torque applied thereon may not beyond acceptance; otherwise the stud might be damaged, and further to damage the entire transducer.

The ultrasonic surgical instrument has to be replaced frequently and the ultrasonic surgical instrument should be assembled in reliable connection every time.

Commonly, the stud of the transducer is typically screwed using a wrench with a constant torque to thereby ensure the stud of the transducer to be connected reliably avoiding being damaged. The wrench is so small and dedicated that it is often lost in use, which makes the entire surgical instrument cannot work. Moreover the wrench is based on elastic deformation of plastic so as to generate a constant torque, but in use the torque varies due to manufacturing errors, material performance differences, and other factors, thus the torque may not be kept constant.

It is disclosed of prior art that a connective structure for connecting a transducer with an ultrasonic surgical instrument, including the transducer and the ultrasonic surgical instrument in threaded connection therewith. The transducer is provided with a stud, and the ultrasonic surgical instrument includes a housing, a waveguide and an end effector, both of which are arranged rotatably in the housing, wherein one end of the waveguide is in connection with the end effector, and the other end is in threaded connection with the transducer; and a protector is further arranged in the housing to make the waveguide rotate together with the stud when the torque reaches a certain threshold while the transducer is being screwed on tightly with respect to the waveguide. The protector includes a block ring, that is arranged in the housing and coaxial with the waveguide, and an elastic ring sleeved fixedly on the waveguide, here a block portion is arranged on an inner wall of the block ring, and an elastic piece portion is arranged on an outer wall of the elastic ring. During the transducer being tightly screwed with respect to the waveguide, when the torque is less than a predetermined value, the block portion is pushed against the elastic portion; when the torque is beyond the predetermined value, the elastic portion goes over the block portion and slip. In this arrangement, although the protector is arranged therein to limit the torque, and is not easy to lose, it may still face the same problem of reliability as the above mentioned wrench may have. Due to slip between the elastic ring and the block ring is caused by self-deformation of material of the block ring and the elastic ring, the torque provided by the protector may significantly vary due to manufacturing errors, material performance differences, material wearing in use, and other factors, thus it may have problems on reliabilities of connection between the transducer and the ultrasonic surgical instrument.

SUMMARY

The disclosure is intended to address such a technical issue of providing an ultrasonic surgical instrument, integrated with a torsion limiting device so as to be connected more conveniently and reliably with a transducer.

In order to address the technical issue above, the disclosure is embodied in the following technical solution of an ultrasonic surgical instrument, the ultrasonic surgical instrument including a waveguide which can rotate around an axis and which is connected with a transducer by screw threads, wherein the ultrasonic surgical instrument further includes a force transmission device and a rotator, the force transmission device is secured to the waveguide, and there is at least one stress face on the force transmission device; and the rotator includes a pushing and pressing mechanism, and a rotatable driving mechanism on which there is at least one applying surface, wherein the stress face and the applying surface are faces which are not perpendicular to the axis and can be engaged with each other, and the pushing mechanism provides a pushing and pressing force to press the rotatable driving mechanism against the force transmission device so that the applying surface is engaged with the stress surface, wherein the pushing and pressing force is arranged such that when a mutually acting force exceeds a predetermined value, the rotatable driving mechanism can overcome the pushing and pressing force so that the applying surface is disengaged from the stress face.

Preferably the rotatable driving mechanism includes a knob body and a knob core, and the knob core non-rotationally but slidably connected to the knob body, the applying surface is arranged on the knob core, and the pushing mechanism is a compressed spring arranged between the knob core and the knob body.

Preferably a plurality of first oblique teeth are arranged on the rotatable driving mechanism, and the applying surface is a ramp of each of the first oblique teeth; and a plurality of second oblique teeth are arranged on the force transmission device, and the stress face is configured as a ramp of each of surface of the second oblique teeth.

Preferably the force transmission device is a force transferring sheath sleeved on the outer surface of the waveguide.

More preferably a wrist pin traverses the force transferring sheath and the waveguide in a radial direction to connect the force transferring sheath and the waveguide together.

Furthermore an inner tube and an outer tube are further arranged in that order between the waveguide and the force transferring sheath, and the wrist pin also traverses the inner tube and the outer tube.

Furthermore a silica sheath is sleeved on the outer surface of the wrist pin.

More preferably a flange extends radically outward from the force transferring sheath, and the stress face is preferably arranged on a side of the flange.

More preferably the rotator is mounted on the force transferring sheath, the knob core can slide axially relative to the force transferring sheath, and a protruding section is arranged on an end portion of the force transferring sheath to block the knob body from sliding axially.

More preferably at least two slide grooves extending axially on an inner wall of the knob body, and sliders protruding radically on the knob core, wherein the sliders are embedded into the slide grooves and slide in cooperation with the slide grooves.

More preferably a knob rubber is arranged on the outer surface of the knob body.

Preferably a connector is further sleeved on the waveguide, and a protection sheath is sleeved on the connector.

More preferably an I-shaped tendon or a cross tendon is arranged on the outer surface of the knob body.

It is another object of the present disclosure to provide an ultrasonic surgical system including any of the ultrasonic surgical instruments, and further including a generator, and a transducer and a control switch, both of which are wired to the generator, wherein the ultrasonic surgical instrument connects the transducer by screw threads.

Preferably the control switch is a foot switch or a hand switch.

The disclosure has the following significant advantageous effects over the prior art: the shears of an ultrasonic surgical instrument according to the disclosure is integrated with the torque limiting device and will not be easily lost. The torque limiting device includes the rotator and the force transmission device, the applying of the rotator and the stress face of the force transmission device are pressed firmly by the pushing mechanism to be engaged together, and the applying surface and the stress face can be oblique teeth arranged circumferentially and engaged with each other. In the disclosure, the torque is transmitted by the acting force (including the pushing force and the frictional force) between the applying surface and the stress face, wherein the magnitude of the frictional force is further determined by the pressing force of the pushing mechanism, so the predetermined torque can be transmitted simply by predetermine the pushing and pressing force reasonably so that when the torque is greater than the predetermined value, the engaged oblique teeth will overcome the pushing and pressing force, and the frictional force and thus skid on each other to thereby limit the torque from being transmitted so as to protect the threads. The operator can load and unload the transducer and rotate the end effector and perform other operations simply and conveniently, simply by rotating the rotator. The disclosure can limit the torque without any deformation of the rotator and the force transmission device, so there will be less requirements on the tolerance, material selection, etc., of the rotator and the force transmission device, the stable pushing and pressing force of the pushing and pressing can guarantee the constant torque, and the pushing and pressing action of the pushing and pressing can also compensate for wearing between the applying surface and the stress face, so the ultrasonic surgical instrument according to the disclosure can be connected more reliably with the transducer of the ultrasonic surgical system. The disclosure can have a better tradeoff between the reliability of the connection and the convenience of the disassembling, and can adjust the angle of the ultrasonic surgical instrument rapidly and conveniently in a procedure to thereby facilitate operations in the procedure, thus the ultrasonic surgical instrument is simple and practical.

Figure 1:
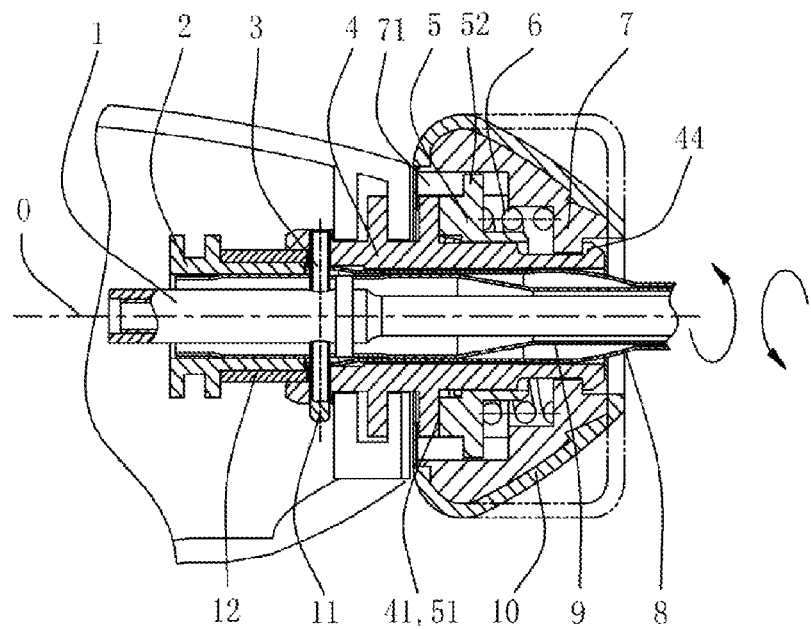
FIG. 1 is a view of an ultrasonic surgical instrument of an ultrasonic surgical system according to the disclosure.

| | | |
|---|---|---|
| 0-axis | 1-waveguide | 2-collar cap |
| 3-wrist pin | 4-force transferring sheath | 5-knob core |
| 6-compressed spring | 7-knob body | 8-outer tube |
| 9-inner tube | 10-knob rubber cover | 11-silica gel sheath |
| 12-protection sheath | 21-buckle | 41-stress surface |
| 42-flange | 43-second oblique tooth | 44-projection |
| 51-applying surface | 52-slider | 53-first oblique tooth |
| 71-slide groove | 72- I-shaped tendon or cross tendon | |
| 91-square groove | | |
| 100-ultrasonic surgical instrument | 200-transducer | 300-generator |
| 400-foot switch | | |

DETAILED DESCRIPTION OF THE EMBODIMENTS

The disclosure will be described below in further details with reference to the drawings and particular embodiments thereof, and those skilled in the art can hereby appreciate other advantages and effects of the disclosure more clearly.

It shall be noted that structures, scales, sizes, etc., illustrated in the drawings are merely intended to illustrate the particular embodiments to enable those skilled in the art to appreciate the idea of the disclosure more clearly but not intended to limit the scope of the disclosure. Any modifications to the structures, changes to proportional relationships or adjustments to the sizes shall fall into the scope of the disclosure without departing from the effects and objects of the disclosure. Relational positional relationships of the respective components will be described with reference to arrangements in the drawings for the sake of easy understanding.

Throughout this description, the term "proximal" will refer to the portion of the instrument closest to the operator and the term "distal" will refer to the portion of the instrument furthest from the operator.

Figure 2:
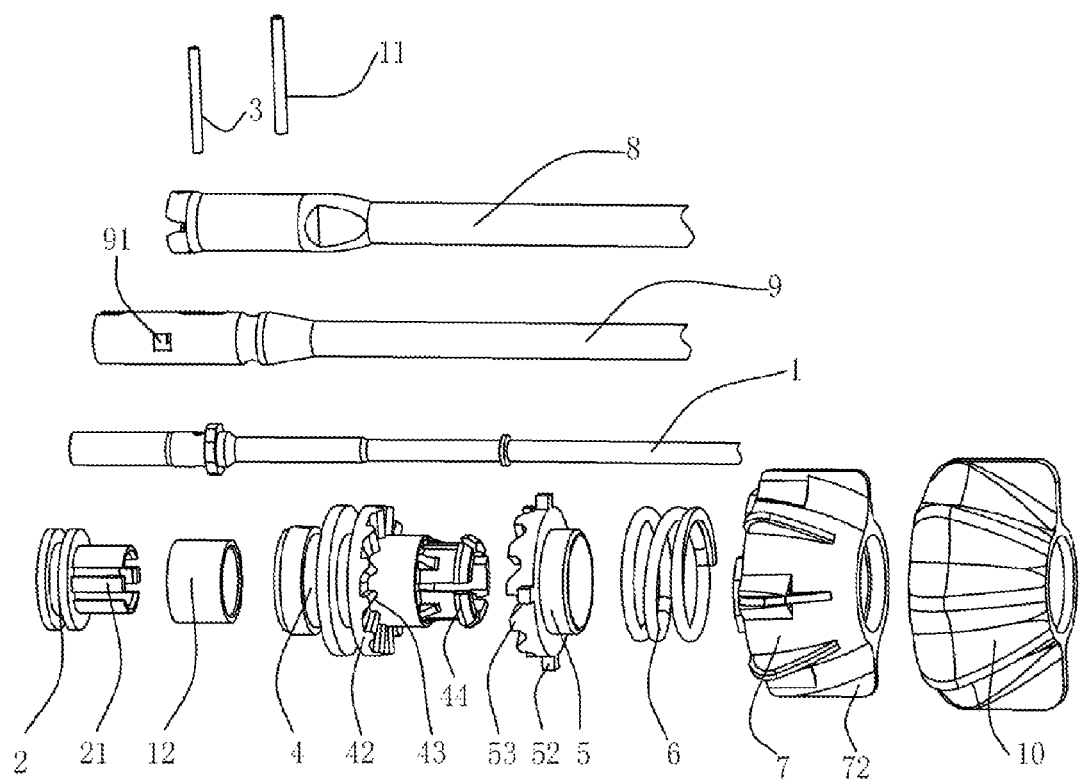
FIG. 2 is an exploded view of the ultrasonic surgical instrument of the ultrasonic surgical system according to the disclosure.

As illustrated in FIG. 1 and FIG. 2, it is disclosed in the present disclosure that an ultrasonic surgical instrument includes a waveguide 1 that is rotatable around an axis 0. The proximal end of the waveguide is provided with a hole having internal threads, adapted for being connected with a transducer, and a force transferring sheath 4 and a rotator are covered outside.

Specifically, the force transferring sheath 4 is one of the embodiments of a force transferring device disclosed herein, adapted for transmitting torque of the rotator to the waveguide 1. The force transferring sheath 4 is in fixed connection with the waveguide 1, and in the preferred embodiment, a wrist pin 3 is disposed through the force transferring sheath 4 and the waveguide 1 radically so as to connect them together. At least one stress surface 41 is provided on the force transferring sheath 4. It is preferred that a flange 42 extends radially outwards from the force transferring sheath 4, and the stress surface 41 is preferably arranged on the flange 42.

The rotator includes a pushing mechanism and a rotatable driving mechanism. There is at least one applying surface 51 provided on the rotatable driving mechanism, here both of the stress surface 41 and the applying surface 51 are not perpendicular to the axis 0 and can be engaged with each other.

In one of the embodiments, the rotatable driving mechanism can be a knob including a knob body 7 and a knob core 5, there are only relative slip along the axis but no relative rotation between the knob body 7 and the knob core 5, so that they can transmit the torque. This connection pattern where they can only side axially but cannot rotate relative to each other can implemented in a spine-like structure. For example, the knob body 7 may be provided with at least two grooves 71 extending axially on the inner wall thereof, and the knob core 5 may be provided with at least two sliders 52, accordingly, protruded radially thereon, wherein the sliders 52 are received in the grooves 71, respectively, and slidable therein. It is preferred that a plurality of first oblique teeth 53 are arranged on one side of the knob core 5, and the applying surface 51 is a ramp of each of the first oblique teeth 53 (referring to FIG. 4); a plurality of second oblique teeth 43 are arranged on the force transferring sheath 4, preferably on the flange 42, and the stress surface 41 is a ramp of each of the second oblique teeth 43 (referring to FIG. 4). A compressed spring 6 is arranged between the distal side of the knob core 5 and the knob body 7 as the pushing mechanism. In alternative embodiments, the pushing mechanism can alternatively be a cylinder, a magnetic-force or electromagnetic-force mechanism, etc. The compressed spring 6 pushes the rotatable driving mechanism (for example, the knob core 5) towards the force transmitting device (for example, the force transferring sheath 4) so that the applying surface 51 is firmly pressed against the stress surface 41. The force provided by the pushing mechanism shall be configured such that when force between the applying surface 51 and the stress surface 41 is in excess of a predetermined value, the rotatable driving mechanism (for example, the knob core 5) can overcome the pushing force so as to make the applying surface 51 skid and disengage with the stress surface 41.

In order to ensure the knob being reliably mounted on the ultrasonic surgical instrument, the knob can be mounted on the force transferring sheath 4 and can axially slide thereon. A plurality of elastic claws are extending from the distal side of the force transferring sheath 4; at least one projection 44 is arranged on the end of each of the elastic claws. The knob body 7 is sleeved on the elastic claws of the force transferring sheath 4, so that the projections 44 can block the knob body 7 from sliding away from the stress surface 41, and the knob can be mounted on the force transferring sheath 4.

In order to facilitate rotation of the knob, an I-shaped tendon or a cross tendon 72 can be arranged on the outer surface of the knob body 7, and a knob rubber cover 10 can be further sleeved on the outside of the knob body 7 to improve hand feeling and increase friction.

In order to perform the function of the ultrasonic surgical instrument normally, an inner tube 9 and an outer tube 8 are further arranged between the waveguide 1 and the force transferring sheath 4 successively, and the wrist pin 3 also disposed there through so as to connect the force transferring sheath 4, the inner tube 9, the outer tube 8, and the waveguide 1 together, wherein the inner tube 9 is provided with an axially elongated groove adapted for being engaged with the wrist pin 3. The wrist pin 3 also may be covered by a silica gel sheath 11 from being loosen after assembling, meanwhile, the silica gel sheath 11 may act as a buffer.

A collar cap 2 is further covered on the proximal end of the inner tube 9, and a protection sheath 12 is covered thereon. An elastic buckle 21 is arranged on the collar cap 2 for being engaged with a square groove 91 of the inner tube 9, and the protection sheath 12 is covered the buckle 21 of the collar cap to prevent the buckle 21 from being bounced. The collar cap 2 is configured to be connected with a drive member, and when the drive member is actuated by the trigger, the collar cap 2 forces the inner tube 9 sliding between the outer tube 8 and the waveguide 1, so as to actuate a pair of jaw members grasping tissues as is known and understood in the art. Therefore no more repeat here.

Figure 3:
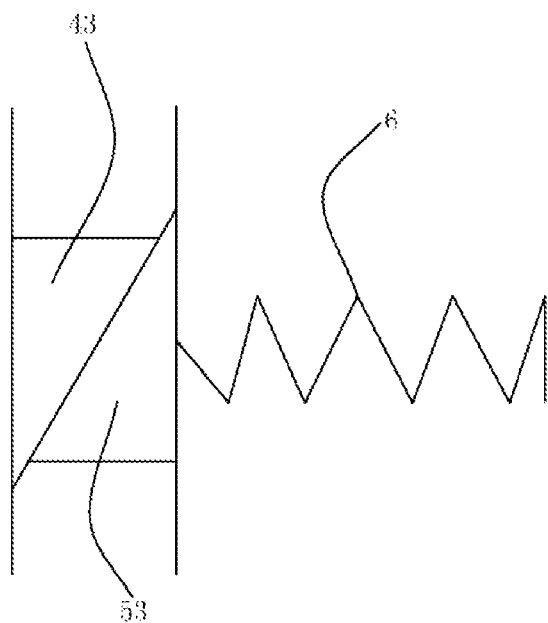
FIG. 3 shows a state where the oblique tooth on the applying surface is normally engaged with the oblique tooth on the stress surface.
Figure 4:
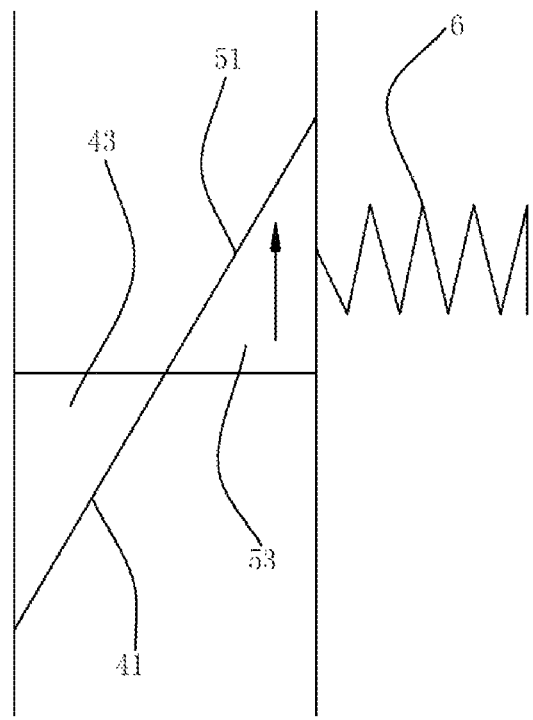
FIG. 4 shows a state where the oblique tooth on the applying surface is sliding with respect to the oblique tooth on the stress surface.

Operations of the ultrasonic instrument according to the disclosure will be described below with reference to FIG. 1, FIG. 3 and FIG. 4 together.

The transducer is assembled by holding the transducer stationary, and rotating the knob rightward. Since the knob core 5 and the force transferring sheath 4 are compressed firmly together by the compressed spring 6, each of the first oblique teeth 53 is normally engaged with each of the second oblique teeth 43 (as illustrated in FIG. 3), and the torque can be transmitted by force (including pushing force and friction) between the stress surface 41 and the applying surface 51 so as to drive the waveguide 1 to rotate rightward. When the torque reaches a predetermined value, the force between the oblique tooth 43 and the oblique tooth 53 is no longer sufficient to transmit the torque, therefore the knob core 5 will overcome the pushing force of the compressed spring 6 and be retracted, thus making the oblique tooth 43 skid with respect to the oblique tooth 53. FIG. 4 shows the state where the oblique tooth 43 is skidding with respect to the oblique tooth 53 and is about to disengage therewith. At this moment, the knob idles, whereas the waveguide 1 does not rotate, which means the transducer has been reliably connected; by limiting the torque between the waveguide 1 and the rotator, the transducer is avoided from being screwed too firmly to damage the threads.

In use, the knob core 5 and the force transferring sheath 4 are compressed firmly together by the compressed spring 6, and the force transferring sheath 4, the inner tube 9, the outer tube 8, and the waveguide 1 all connected by the wrist pin 3 can rotate together, so that the operator can rotate the knob with his/her finger(s) while no extra force is applied to the transducer, so as to rotate the knob, the inner and outer tubes, and other members freely, that is, adjust the angle of the end effector freely.

Figure 5:
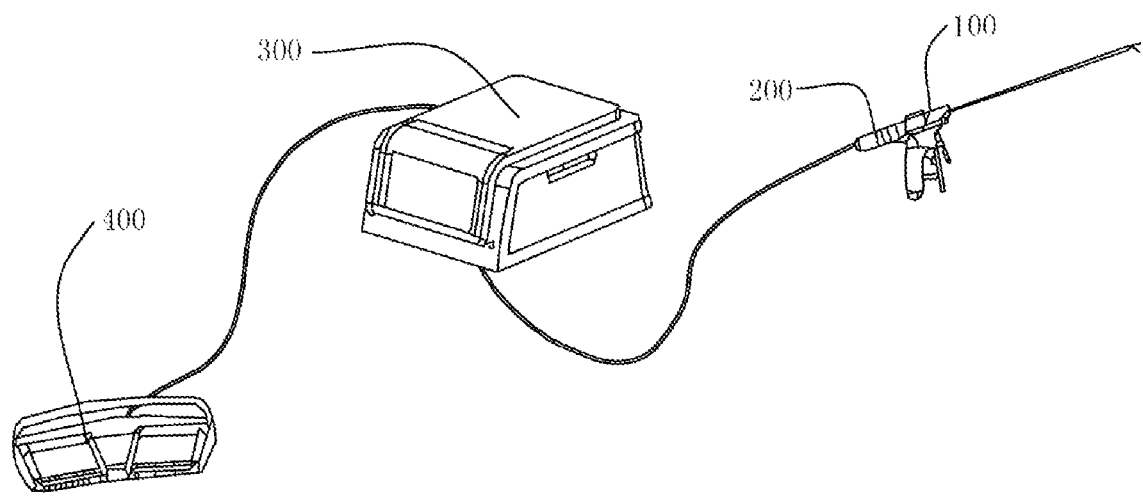
FIG. 5 is a view of the ultrasonic surgical system.

Referring to FIG. 5, as one of the embodiments of the present disclosure, an ultrasonic surgical instrument 100 as described above is in threaded connection with a transducer 200, and the transducer 200 and a foot switch 400 are in connection with a generator 300 via cables. The foot switch 400 can alternatively be replaced by a hand switch arranged on the ultrasonic surgical instrument 100 to actuate the ultrasonic surgical instrument.

Of course, the foregoing disclosure is merely illustrative of particular application examples of the disclosure but not intended to limit the scope of the disclosure in any sense. The disclosure can also be embodied in other embodiments than the embodiments above. Any modifications or variations thereto without departing from the spirit of the disclosure shall fall into the scope of the disclosure as defined in the depended claims.

The invention claimed is:

1. An ultrasonic surgical instrument, comprising a waveguide rotatable around an axis and in threaded connection with a transducer, wherein said ultrasonic surgical instrument further comprises a force transmission mechanism and a rotatable mechanism; said force transmission mechanism is in fixed connection with said waveguide, provided with at least one stress surface thereon; said rotatable mechanism comprises a pushing mechanism and a rotatable driving mechanism having at least one applying surface thereon; said stress surface and said applying surface are not perpendicular to said axis and can be engaged with each other; said pushing mechanism provides a pushing force to press said rotatable driving mechanism towards said force transmission mechanism so as to force said stress surface being engaged with said applying surface; said pushing force is configured such that when a force between said stress surface and said applying surface is in excess of a predetermined value, said rotatable driving mechanism can overcome said pushing force so as to make said stress surface disengage with said applying surface.

2. The ultrasonic surgical instrument according to claim 1, wherein said rotatable driving mechanism comprises a knob body and a knob core in no-rotatable connection therewith, and said knob core can slide with respect to said knob body along said axis; said stress surface is arranged on said knob core, and said pushing mechanism is configured as a compressed spring arranged between said knob core and said knob body.

3. The ultrasonic surgical instrument according to claim 2, wherein said force transmission mechanism is a force transferring sheath covered outside said waveguide.

4. The ultrasonic surgical instrument according to claim 3, wherein a wrist pin is disposed through said force transferring sheath and said waveguide in radial direction so as to connect said force transferring sheath and said waveguide together.

5. The ultrasonic surgical instrument according to claim 4, wherein an inner tube and an outer tube are further arranged between said waveguide and said force transferring sheath successively, and said wrist pin is disposed therethrough.

6. The ultrasonic surgical instrument according to claim 4, wherein a silica gel sheath is covered outside said wrist pin.

7. The ultrasonic surgical instrument according to claim 3, wherein a flange is arranged on said force transferring sheath extending radially outwards, and said stress surface is arranged on an end of said flange.

8. The ultrasonic surgical instrument according to claim 3, wherein said rotatable mechanism is mounted on said force transferring sheath; said knob core can axially slide with respect to said force transferring sheath, and at least one projection is arranged on an end of said force transferring sheath to block said knob body from sliding axially.

9. The ultrasonic surgical instrument according to claim 2, wherein said knob body is provided with at least two grooves extending radially from an inner wall thereof; said knob core is provided with at least one slider accordingly, wherein, said slider is received in said grooves respectively and slidable therein.

10. The ultrasonic surgical instrument according to claim 2, wherein a knob rubber cover is arranged on said outer surface of said knob body.

11. The ultrasonic surgical instrument according to claim 2, wherein an I-shaped tendon or a cross tendon is arranged on said outer surface of said knob body.

12. The ultrasonic surgical instrument according to claim 2, wherein a plurality of first oblique teeth are arranged on said rotatable driving mechanism, and said stress surface is configured as a ramp of each of said first oblique teeth; and a plurality of second oblique teeth are arranged on said force transmission mechanism, and said applying surface is configured as a ramp of each of said second oblique teeth.

13. The ultrasonic surgical instrument according to claim 1, wherein a plurality of first oblique teeth are arranged on said rotatable driving mechanism, and said stress surface is configured as a ramp of each of said first oblique teeth; and a plurality of second oblique teeth are arranged on said force transmission mechanism, and said applying surface is configured as a ramp of each of said second oblique teeth.

14. The ultrasonic surgical instrument according to claim 1, wherein a collar cap is further coupled with said waveguide, and a protection sheath is covered said collar cap.

15. An ultrasonic surgical system, comprising an ultrasonic surgical instrument, wherein the ultrasonic surgical instrument comprising, a waveguide rotatable around an axis and in threaded connection with a transducer, wherein said ultrasonic surgical instrument further comprises a force transmission mechanism and a rotatable mechanism; said force transmission mechanism is in fixed connection with said waveguide, provided with at least one stress surface thereon; said rotatable mechanism comprises a pushing mechanism and a rotatable driving mechanism having at least one applying surface thereon; said stress surface and said applying surface are not perpendicular to said axis and can be engaged with each other; said pushing mechanism provides a pushing force to press said rotatable driving mechanism towards said force transmission mechanism so as to force said stress surface being engaged with said applying surface; said pushing force is configured such that when a force between said stress surface and said applying surface is in excess of a predetermined value, said rotatable driving mechanism can overcome said pushing force so as to make said stress surface disengage with said applying surface, the ultrasonic surgical system further comprising a generator, and a transducer and a controlling switch, both of which are wired to said generator, wherein said ultrasonic surgical instrument is in threaded connection with said transducer.

16. The ultrasonic surgical system according to claim 15, wherein said controlling switch is a foot switch or a hand switch.

17. The ultrasonic surgical system according to claim 15, wherein said rotatable driving mechanism comprises a knob body and a knob core in no-rotatable connection therewith, and said knob core can slide with respect to said knob body along said axis; said stress surface is arranged on said knob core, and said pushing mechanism is configured as a compressed spring arranged between said knob core and said knob body.

18. The ultrasonic surgical system according to claim 17, wherein said force transmission mechanism is a force transferring sheath covered outside said waveguide.

19. The ultrasonic surgical system according to claim 18, wherein a wrist pin is disposed through said force transferring sheath and said waveguide in radial direction so as to connect said force transferring sheath and said waveguide together.

20. The ultrasonic surgical system according to claim 15, wherein a plurality of first oblique teeth are arranged on said rotatable driving mechanism, and said stress surface is configured as a ramp of each of said first oblique teeth; and a plurality of second oblique teeth are arranged on said force transmission mechanism, and said applying surface is configured as a ramp of each of said second oblique teeth.

\* \* \* \* \*